(12) United States Patent
Rahmani

(10) Patent No.: US 8,211,435 B2
(45) Date of Patent: Jul. 3, 2012

(54) CALF BIOLOGIC ANTI-SCOUR SUPPLEMENT (CBAS)

(76) Inventor: Hamid Reza Rahmani, Isfahan (IR)

( * ) Notice: Subject to any disclaimer, the term of this patent is extended or adjusted under 35 U.S.C. 154(b) by 347 days.

(21) Appl. No.: 12/480,713

(22) Filed: Jun. 9, 2009

(65) Prior Publication Data

US 2009/0246207 A1    Oct. 1, 2009

(51) Int. Cl.
| | | |
|---|---|---|
| A61K 39/395 | (2006.01) | |
| A61K 39/00 | (2006.01) | |
| A61K 39/38 | (2006.01) | |
| A61K 45/00 | (2006.01) | |
| A61K 47/00 | (2006.01) | |

(52) U.S. Cl. ............... 424/157.1; 424/130.1; 424/184.1; 424/278.1

(58) Field of Classification Search ........................ None
See application file for complete search history.

(56) References Cited

U.S. PATENT DOCUMENTS

2009/0246207 A1* 10/2009 Rahmani .................... 424/157.1

OTHER PUBLICATIONS

Uruakpa et al, Nutrition Research, 2002, 22:755-767.*
Pakkanen et al, Int. Dairy Journal, 1997, 7:285-297.*
Mehra et al, International Dairy Journal, 2006, 16:1262-1271.*
Joslin et al, J. Dairy, Sci, 2002, 85:1237-1242.*
Rob Costello, Merrick's, Calf Scours, 2005, pp. 1-4.*
Kelly, Alternative Medicine Review, 2003, 8/4:378-394.*
Struff et al, International Journal Clinical Pharmacology and Therapeutics, 2008, 46/5:211-225.*
Schnepper, Calf Talk, Feb. 2008, 14/2:1 page.*

* cited by examiner

*Primary Examiner* — Nita M Minnifield
(74) *Attorney, Agent, or Firm* — Barry Choobin; Choobin & Choobin Consultancy

(57) ABSTRACT

A composition for prevention digestive infection in a ruminant infant is disclosed. The composition consists of: a predetermined amount of yolk immunoglobulin (IgY) for a target bacteria; a predetermined amount of a plurality of hormones and a predetermined amount of a plurality of proteins, wherein said plurality of hormones comprises of a group consisting of bovine insulin (bIns), bovine growth hormone (bGH), and bovine prolactine (bPrl), and wherein said plurality of proteins comprises of a group consisting of, bovine insulin like growth factor (bIGF), lactoferrin factor (LF), and transferring factor (TF); and a predetermined amount of bacterial biomass, wherein said bacterial biomass comprises of a group consisting of bacterial DNA, bacterial RNA, bacterial protein, and bacterial polysaccharides.

5 Claims, No Drawings

CALF BIOLOGIC ANTI-SCOUR SUPPLEMENT (CBAS)

SPONSORSHIP STATEMENT

The present invention is Sponsord by Iranian National Science Foundation and Isfahan University of Technology (IUT) of Iran for International filing.

FIELD OF THE INVENTION

The present invention pertains to the animal production and dairy farming, more particularly, to the prevention of calf and lamb scour by adding biologically prepared immunoglobulins, hormones and factors to the colostrum.

BACKGROUND OF THE INVENTION

Colostrum as a natural product synthesized in the mammary gland of mammalians has been known the most important source of nutrients and immunoglobulins for infants, particularly in ruminants for many years. In ruminants, at the parturition time the digestive system of infants is not developed completely and needs to be matured morphologically and functionally. This developmental process is essential for a transition from blood nutrition to digestive nutrition and more importantly adaptation to the environment. Colostrum as the main source of nutrients and non-nutrients has the key role in this situation. The transition period for the infants includes the metabolic, hormonal and immunological status which is significantly dependent to colostrum components.

Colostrum as the primary milk contains considerable amount of essential fatty acids, essential amino acids, minerals, essential trace elements, pre-vitamins, fat and water soluble vitamins, non-nutrient components (immunoglobulins and anti-bacterial substances), epithelial cells (lactocytes), erythrocytes and leukocytes. Most of the non-nutrient and bioactive compounds of the cow's colostrum is derived from the maternal blood including Gl (immunoglobulin gamma), GH (growth hormone), Prl (prolactin), Ins (insulin) and Glu (glucagon). Other colostral factors are derived from the lactocytes of the mammary gland which includes IGF-I binding proteins, and peptides and proteins. Casein and lactose are couple of important nutrients which come to the milk after colostrum production. But, recently it has been shown which there are many other considerable components in the colostrum of ruminants such as releasing factors (RF), growth factors (GF), cytokines, prostaglandins (PG), enzymes, lactoferrin (LF), transferrin (TF), nucleotides, polyamines and oligosaccharides. The interesting point in this relation is the species dependency and difference between the concentration of these components in different animals, particularly ruminants, and their significant decline after 24 hours after parturition.

Reviewing the history of researches done on the colostrum reveals a new world in this case which has been gradually completed. In 1976 the specific effect of colostral components on morphological changes of calf digestive system was shown. Afterward in 1978, the existence of mitogenic materials in the colostrum and it's difference in different species was discovered. The effect of these components on cell proliferation, immigration, differentiation and apoptosis of the digestive epithelium, and also protein synthesis, digestion, absorption, motility and immune system of gastrointestinal tract of calves made a special field of research. Metabolism, endocrine, vascular tone, homeostasis, growth and behavior of the calf and lamb are other studied parameters in this regard. Ruminant infants are pseudo-monogastric at the birth time, and their digestive system is developed very quickly which are due to be a real ruminant after several weeks. This development is also related to accessory organs of the GIT such as pancreas and liver, which enables the infants to stop pinocytotic absorption and start cellular digestion in a week. Any deficiency in this mechanism which is dependent to the non-nutrient components of the colostrum makes a serious problem. It has been shown the early hours of the birth are very crucial time for these physiological changes for the digestive system, and colostral non-nutrient components are able to stimulate the epithelial cells to grow. It has been suggested different mechanisms for maturation of digestive system in ruminant infants which covers paracrine, autocrine and endocrine systems for luminokines, gastrin, cholecystokinin, secretin, VIP, motilin, pancreatic poly peptide, somatostatin, IGF-I and insulin of the colostrum.

Recent studies in this field reveal the colostrum dependency of digestive immune system, particularly the lymphocyte development by involving the hormonal and growth factors existing in the colostrum. This pattern is also copied by adding the IGF-I prepared from transgenic bacteria.

There are many other researches in this field which is out of the scope of this application, but some of them are registered as international patents which is necessary to be mentioned. Scour is a serious disease or syndrome of infants which have been under investigation for many years and many natural and synthetic anti-scour drugs and compounds have been suggested for it's prevention or treatment. The registered patents in this case numbered U.S. Pat. Nos. 4,192,886, 4,285,972, 4,332,814, 4,520,014, 5,080,895, 5,795,602, 5,928,640, 6,066,341, 6,291,449, 6,365,152, 6,495,567, 6,967,090, 6,974,577, 7,045,149, 7,252,836, 7,309,493, 7,371,401 and 7,384,628 since 1980 to 2008 are just registered in the USA over three decades. All these patents show an evolution of different methods for fighting against the scour syndrome, particularly in ruminant infants. The noticeable point is the substitution of natural products for antibiotics in recent years to prevent the human concern about antibiotic resistance.

Regarding all the details in the patents and their products reveal different point of view as looking for an effective anti-scour material. As I tried searching and thinking in this field I more focused on the overall idea of all these patents and searching the basic cause of scour in ruminant infants, and finally to enrich the probable deficiency of the colostrum by using natural components. In this case, this research from the beginning to the end and claiming the invention took five years and five different stages of experiments.

SUMMARY OF THE INVENTION

The principal objective of the present invention is to provide a method for prevention digestive infection in a ruminant infant comprising steps of: adding a predetermined amount of biologic materials to maternal natural colostrum wherein said biological materials consists of: a predetermined amount of yolk immunoglobulin (IgY) for a target bacteria; a predetermined amount of a plurality of hormones and a predetermined amount of a plurality of proteins, wherein said plurality of hormones comprises of a group consisting of bovine insulin (bIns), bovine growth hormone (bGH), and bovine prolactine (bPrl), and wherein said plurality of proteins comprises of a group consisting of, bovine insulin like growth factor (bIGF), lactoferrin factor (LF), and transferring factor (TF); and a predetermined amount of bacterial biomass, wherein said bacterial biomass comprises of a group consisting of bacterial DNA, bacterial RNA, bacterial protein, and bacterial polysaccharides.

Yet another object of the present invention is to provide a composition for prevention digestive infection in a ruminant infant wherein said composition consists of: a predetermined amount of yolk immunoglobulin (IgY) for a target bacteria; a predetermined amount of a plurality of hormones and a predetermined amount of a plurality of proteins, wherein said plurality of hormones comprises of a group consisting of bovine insulin (bins), bovine growth hormone (bGH), and bovine prolactine (bPrl), and wherein said plurality of proteins comprises of a group consisting of, bovine insulin like growth factor (bIGF), lactoferrin factor (LF), and transferring factor (TF); and a predetermined amount of bacterial biomass, wherein said bacterial biomass comprises of a group consisting of bacterial DNA, bacterial RNA, bacterial protein, and bacterial polysaccharides.

Stage 1: Investigation the Colostrum Components Deficiency

As already mentioned the basic hypothesis was deficiency of some important factors in the colostrum as the cause of 10-25% diarrhea and mortality in dairy farm infants.

Materials and Methods

Two good managed industrial farms in Esfahan province and three farms in Tehran province were selected. 500 cows were randomly selected for colostrum sampling as each farm had 100 cows under the experiment. The cows in each farm were divided in 5 groups regarding their parity ($1^{st}$, $2^{nd}$ and more) and their drying period (40±5, 60±5 days) for multiparous cows as each group had at least 15 cows for primiparous and 20 for multiparous groups. Colostrum was collected from dairy cows at 0, 12 and 24 hours after parturition time, the calf blood samples were collected after the birth and 3 days after birth in vacutainer tubes with EDTA as anti-coagulant. Colostrum samples were kept at −20° C. for 2 months and were analyzed for IgG, Insulin (Ins), Glucagon (Glu), Growth Hormone (GH), Prolactin (Prl), IGF-I, II, Transferrin (TF) and Lactoferrin (LF). Somatic cell count (SCC), pH and microbial content of the colostrums were other factors which were analyzed and recorded. Calf blood samples were centrifuged and their plasma were collected and kept at −20° C. and analyzed for IgG, total protein and albumin and globulin ratio. Other factors such as birth weight, daily weight gain, weekly weight gain, calf height and it's growth, feces score, diarrhea, treatment, weaning time, starter consumption and performance factors were also recorded. The data were analyzed by GLM method using SAS program, and the mean values were compared by Duncan's multiple range test, and mentioned significant at P<0.01 value.

Results of this part are not reported in detail, because the paper has not been published yet and is waiting for patent registration. Briefly, the analyzed data showed the parity, drying period, SCC and microbial content of the colostrum affected the mentioned colostral components significantly (P<0.01). Decline of these factors differed from 30 to 60 percent depending on the status and physiological circumstances of the cattle in the farm. There was a positive and significant correlation between the colostral components deficiency and scour syndrome or symptoms and negative fecal score.

Stage 2: Preparing the *E. coli* Antibody in the Egg

As the clinical and microbial investigation shows there are 3 kinds of *E. coli* serotypes which have the most infection in calves. Preparing the antibody for recovering the colostral deficiency was an important stage and the results of several researches had shown it was possible by immunizing the rabbit, goat or laying chicken. The last one seemed more economic and logic. The leghorn laying hen were immunized by 2 most known *E. coli* serotypes four times over 4 weeks and their serum and egg yolk were collected after 3 weeks of injection and their antibody against the specific *E. coli* were measured by ELISA method in the serum and egg yolk. The results showed the raising significant amount of specific antibody in the egg yolk after 4 weeks and maintaining high till 8 weeks after injection. The collected egg yolk were partially purified for antibody separation by WSF method, and the bulk amount of antibody were collected and measured for final use in stage 4 of the experiment.

Stage 3: Preparing the Hormones from Transgenic *E. coli*

Genetic engineering has made the opportunity to produce different peptides in the microorganisms. In this part of the invention the transgenic bacteria (*E. coli*) were used for production of hormones such as, bovine (b) bGH, bIGF-I, II, bPrl and bIns, and the biomass product was collected from the fermantor and it's hormonal content evaluated by RIA method. This point should be mentioned which the biomass also contained bacterial (B) DNA, RNA and a few amount of phosphate buffer saline (PBS) as the washing solution for centrifugation. LF and TF were also purchased for adding to the colostrum. Regarding our experience *E. coli* bacterial stock survived for 12-14 passages producing hormones so the stock were kept as the main source and subcultures used for hormone production purposes. The fermantor condition and the other factors for optimum microbial production were optimized, and the results of this part are also secret of the invention which would be disclosed after hope of registration. The amount of each factor needed for colostral enrichment was evaluated and measured from the results of the $1^{st}$ stage of the research. There was just a concern about the bacterial polysaccharides, DNA and RNA in the final solution which a few papers and patents and also my contact with other scientists confirmed it's usefulness rather than danger. At last the solution evaluated which contained several components (IgY, bIns, bGH, bPrl, bIGF-I, II, BDNA, BRNA, Bprot., BPS, LF, TF and PBS; pH 7.2) was ready as the main solution for colostrum enrichment and called CBAS (Calf Biologic Anti-Scour Supplement), because all the components were prepared by biological methods and expected to be useful in development of the ruminant infants digestive system and preventing the diarrhea.

Stage 4: Packaging and Storing of the CBAS

Next part of the project involved the form of offering the product and also it's packaging. At the beginning the final solution was stored at 4° C. and it's content was evaluated after 24 and 72 hours. The results showed significant decline of the mentioned factors, and was not promising. The other problem was negative effect of light and the form of packing in the glass or plastic which were also effective on the half life of the proteins. Finally a trial was run with different packaging and storing condition forms, which revealed the 3 layers (one aluminum and two polyethylenes, inside and outside which is the best form of packaging, and −15° C. is the best storing condition for maximum 6 months to keep the proteins at the same level of production time. So the CBAS was prepared and packed for the final part of the project and kept in the freezer at −17° C.

Stage 5: Enrichment of the Colostrum by CBAS

This stage of the project was using the final products in colostrum as the enrichment compound. Ninety calves in two different farms (45 each) were randomly selected with average weight 45±3 kg and were divided in 3 groups; group 1 (control, n=15) with maternal colostrum without additional content, group 2 (carrier control, n=15) with carrier (15 ml of milk and 3 ml of PBS, as the CBAS carrier), and group 3 (treatment, n=15) with the complete CBAS. Groups 2 and 3 received the CBAS and it's carrier for the first 5 days after parturition time with their morning colostrum or milk. Calves were under the control and record program for physiological circumstances after the parturition time. As mentioned in the $1^{st}$ stage the blood samples were also collected from the calves at 0, 1, 3 day, and weaning time of their life, and other mentioned performance factors were daily recorded. The data were analyzed by the GLM method as the completely random design test, and the mean values were compared by Duncan's multiple range test using the SAS program software.

Results of the performance of the calves from this part of the project are summarized in Table 1. The results of blood parameters and it's scientific discussion are to be published after the patent registration. As the Table 1 shows all the parameters are influenced by the treatment significantly (P<0.01), particularly the incidence of the scour. As the body weight (BW) of the three groups were identical at the beginning of the experiment after 3 and 6 weeks showed significant difference between groups.

Other parameters such as health conditions, fecal score, day of feeding starter, starter consumption rate of day 50 and weaning day were also affected by treatment.

TABLE 1

Calf performance parameters (Mean ± SEM) over the 3 months experiment

| Calf status | Group | | |
|---|---|---|---|
| | 1 (control) | 2 (CBAS carrier) | 3 (CBAS) |
| IBW (kg) | 45 ± 3$^a$ | 44 ± 3$^a$ | 45 ± 3$^a$ |
| BWG (kg) 0-3 week | 5.2 ± 1.5$^b$ | 5.4 ± 1.3$^b$ | 8.2 ± 2.4$^a$ |
| BWG (kg) 3-6 week | 8.6 ± 2.1$^b$ | 7.4 ± 3.1$^b$ | 10.7 ± 2.6$^a$ |
| Scour (days) | 4.2 ± 1.5$^b$ | 4.7 ± 1.3$^b$ | 0.75 ± 0.25$^a$ |
| Health (%) | 38$^b$ | 40$^b$ | 78$^a$ |
| Fecal score (1-5) | 1.54 ± 0.65$^b$ | 1.75 ± 0.45$^b$ | 3.65 ± 0.83$^a$ |
| Day of starter feeding | 17 ± 2$^b$ | 16 ± 2$^b$ | 8 ± 3$^a$ |
| Starter consumption on day 50 | 0.83 ± 0.16$^b$ | 0.87 ± 0.15$^b$ | 1.4 ± 0.2$^a$ |
| Weaning time (day) | 70 ± 3$^b$ | 72 ± 4$^b$ | 50 ± 3$^a$ |

Different superscript letters in each row means significant difference between the Mean ± SEM (P < 0.01)
IBW; Initial Body Weight
BWG; Body Weight Gain The invention has been described in connection with its preferred embodiments. However, it is not limited thereto. Changes, variations and modifications to the basic design may be made without departing from the inventive concepts in this invention. In addition, these changes, variations and modifications would be obvious to those skilled in the art having the benefit of the foregoing teachings. All such changes, variations and modifications are intended to be within the scope of the invention which is limited only by the following claims.

I claim:

1. A composition for prevention of digestive infection in a ruminant infant wherein said composition consists of:
   a predetermined amount of yolk immunoglobulin (IgY) for a target bacteria;
   a predetermined amount of a plurality of hormones and a predetermined amount of a plurality of proteins, wherein said plurality of hormones consists of bovine insulin (bIns), bovine growth hormone (bGH), and bovine prolactin (bPrl), and wherein said plurality of proteins consists of bovine insulin like growth factor (bIGF), lactoferrin (LF), and transferrin (TF); and
   a predetermined amount of bacterial biomass, wherein said bacterial biomass consists of bacterial DNA, bacterial RNA, bacterial protein, and bacterial polysaccharides.

2. The composition as claimed in claim 1, wherein said composition is preserved with a plurality of layers wherein said plurality of layers consists of one aluminum layer and two polyethylene layers.

3. The composition as claimed in claim 1, wherein said composition is stored at −15° C.

4. The composition as claimed in claim 1, wherein said composition is stored for up to 6 month without changing.

5. A method for preventing digestive infection in a ruminant infant comprising administering to said ruminant infant maternal natural colostrum and the composition of claim 1.

* * * * *